(12) United States Patent
Cabot (10) Patent No.: US 11,007,062 B2
(45) Date of Patent: May 18, 2021

(54) ARRANGEMENT AND METHOD IN THE PREPARATION OF THE DISTAL FEMUR AND POSTERIOR FEMORAL CONDYLE PROXIMAL SURFACES OF THE FEMUR FOR THE FEMORAL COMPONENT OF A PROSTHETIC KNEE JOINT

(71) Applicant: Jonathan Peter Cabot, North Adelaide (AU)

(72) Inventor: Jonathan Peter Cabot, North Adelaide (AU)

( * ) Notice: Subject to any disclaimer, the term of this patent is extended or adjusted under 35 U.S.C. 154(b) by 0 days.

(21) Appl. No.: 16/302,272

(22) PCT Filed: May 19, 2017

(86) PCT No.: PCT/AU2017/050468
§ 371 (c)(1),
(2) Date: Nov. 16, 2018

(87) PCT Pub. No.: WO2017/197462
PCT Pub. Date: Nov. 23, 2017

(65) Prior Publication Data
US 2019/0216608 A1    Jul. 18, 2019

(30) Foreign Application Priority Data

May 19, 2016  (AU) ................................ 2016901872
May 19, 2017  (WO) ................. PCT/AU2017/050468

(51) Int. Cl.
*A61F 2/38* (2006.01)
*A61F 2/46* (2006.01)
*A61F 2/30* (2006.01)

(52) U.S. Cl.
CPC ............ *A61F 2/3859* (2013.01); *A61F 2/389* (2013.01); *A61F 2/46* (2013.01); *A61F 2/4657* (2013.01);
(Continued)

(58) Field of Classification Search
CPC .. A61F 2/46; A61F 2/4657; A61F 2002/4661; A61F 2002/4658; A61F 2/461;
(Continued)

(56) References Cited

U.S. PATENT DOCUMENTS 5,860,980 A * 1/1999 Axelson, Jr. ......... A61B 17/155
                                                     606/88
7,442,196 B2 * 10/2008 Fisher .................... A61B 17/02
                                                     606/88
(Continued)

FOREIGN PATENT DOCUMENTS

WO    2009006741    1/2009
WO    2011127477    10/2011

*Primary Examiner* — Matthew J Lawson
*Assistant Examiner* — Lisa Nguyen
(74) *Attorney, Agent, or Firm* — Renner Kenner Greive Bobak Taylor & Weber (57) ABSTRACT

An arrangement for providing the proximal surface of the distal end of the femur and the posterior femoral condyle of the femur for a femoral component of a prosthetic knee joint, said arrangement including an alignment clamp mountable to the femur such that a vertical arm of the alignment clamp includes user-operable lateral adjustable extension tabs and a horizontal arm of the alignment clamp that includes user-operable height adjustable extension tabs wherein the lateral and height adjustable tabs engage with a front plate and a base plate which define out reference planes and/or an axis that can be used in establishing the alignment for the definitive resection cuts to the distal end of the femur and the posterior femoral condyle of the femur.

8 Claims, 4 Drawing Sheets

(52) U.S. Cl.
 CPC ....... *A61F 2/38* (2013.01); *A61F 2002/30556* (2013.01); *A61F 2002/4658* (2013.01)
(58) Field of Classification Search
 CPC .......... A61B 2017/0268; A61B 17/154; A61B 17/155; A61B 17/157; A61B 17/1764
 See application file for complete search history.

(56) References Cited

U.S. PATENT DOCUMENTS

| | | | |
|---|---|---|---|
| 2005/0177169 A1* | 8/2005 | Fisher .................... | A61F 2/4684 606/88 |
| 2010/0063508 A1* | 3/2010 | Borja .................... | A61B 17/154 606/88 |

* cited by examiner

ARRANGEMENT AND METHOD IN THE PREPARATION OF THE DISTAL FEMUR AND POSTERIOR FEMORAL CONDYLE PROXIMAL SURFACES OF THE FEMUR FOR THE FEMORAL COMPONENT OF A PROSTHETIC KNEE JOINT

FIELD OF THE INVENTION

This invention relates to an arrangement and method in the preparation of the femoral surface for the femoral component of a prosthetic knee joint.

More particularly this invention relates to the preparation of the distal femur and posterior femoral condyle proximal surfaces of the femur such that the final bone resection of the femur provides balanced stability between the femoral component and the tibia component of the prosthetic knee joint to permit stable and balanced movement throughout the knee joint's angular movement from extension, mid-flexion and through to flexion and then back again.

BACKGROUND ART DISCUSSION

Knee replacement implants are artificial devices that are used to replace a damaged knee or a part of a knee thereof.

A damaged knee joint will contain a combination of bone structure and multiple soft tissue groupings and depending upon where the knee damage arrived from, whether rheumatoid arthritis, osteoarthritis and/or traumatic or other injury, means that every knee replacement or partial knee replacement will either be, if not substantially, at least subtly different albeit ultimately the artificial implants used in the knee replacement will be for the most part of standard sizes.

While an objective of any knee replacement utilising implants would look for an exact reproduction of the structure and operation of a normal healthy knee, as introduced above such a scenario would be very difficult to achieve given the potential differing degrees in the severity of damage to the knee joint and the differences of an individual's bone structures to another.

During surgery, an orthopaedic surgeon when replacing a damaged knee with replacement implants will be required to prepare those bone structures involved in the knee joint to accept the artificial implant including the distal end of the femur, the proximal surface of the tibia and the patella.

This invention focuses on the upper half of the knee joint, specifically the proximal surface of the femur connected with the distal femur and the posterior femoral condyle. The correct positioning of the femoral component of the prosthetic knee joint upon the distal femur and the posterior femoral condyle in conjunction with an appropriately aligned tibia component assists in providing the best long term balanced and stable prosthetic knee joint.

It is recognised that the level and/or angle of the final bone resection of the distal femur and the posterior femoral condyle of the femur assists in the correct alignment of the femoral component of the prosthetic knee joint to establish an appropriate gap between both the tibial component and the femoral component to ensure stable and secure balanced movement of the knee joint.

Accordingly it is an object of this invention to provide an arrangement and method such that the final resected cuts of the distal femur and the posterior femoral condyle of the femur provide a surface profiling of the bone for optimum femoral component positioning in the total knee arthroplasty such that there is stable and balanced movement between the femoral component and the tibial component in the prosthetic knee joint throughout the arc of motion of the knee from extension, mid-flexion through to flexion.

Further objects and advantages of the invention will become apparent from a complete reading of this specification.

SUMMARY OF THE INVENTION

In one form of the invention there is provided an arrangement for providing the proximal surface of the distal end of the femur and the posterior femoral condyle of the femur for a femoral component of a prosthetic knee joint, said arrangement including:

a generally L shaped femoral tibia stability gap alignment clamp mountable to the femur such that a vertical arm of the generally L shaped femoral tibia gap alignment clamp is adapted to be contiguous and/or aligned with the distal end of the femur and a horizontal arm of the generally L shaped femoral tibia gap alignment clamp is adapted to be contiguous and/or aligned with a posterior femoral condyle of the femur;

said vertical arm of the generally L shaped femoral tibia stability gap alignment clamp including user-operable lateral adjustable extension tabs, wherein each user-operable lateral adjustable extension tab is adapted to engage a front plate, such that lateral adjustment of the front plate by said plurality of user-operable lateral adjustable extension tabs defines a first stability gap as a measurement taken in each of extension, mid-flexion and flexion, wherein the first stability gap is commensurate with a reference plane defined by the front surface of the front plate, wherein a final bone resection with the reference plane defined by the front surface of the front plate to a distal end of the femur provides balanced angular movement between the tibia component and the femoral component of the prosthetic knee joint throughout an arc of motion from extension, mid-flexion and flexion post surgery;

said horizontal arm of the generally L shaped femoral tibia stability gap alignment clamp includes user-operable height adjustable extension tabs adapted to adjust the vertical height of a base plate relative to the horizontal arm of the generally L shaped femoral tibia stability gap alignment clamp, such that vertical height adjustment of said plurality of user-operable height adjustable extension tabs upon the base plate defines a second stability gap as a measurement taken in each of extension, mid-flexion and flexion, wherein the second stability gap is commensurate with a referenced axis or plane defined on an underside of the base plate, wherein final bone resection with the referenced axis or plane defined on an underside of the base plate to the posterior femoral condyle of the femur provides for balanced angular movement between the femoral component and the tibia component of the prosthetic knee joint throughout an arc of motion from extension, mid-flexion and flexion.

In preference the front plate is commensurate in dimensions with the dimensions and shape of the distal end of the femur.

In preference the base plate includes separate sections, wherein each section of the base plate is positionable below a corresponding user-operable height adjustable extension tab adapted to adjust the vertical height of the respective separated sections of the base plate relative to the horizontal arm of the generally L shaped femoral tibia stability gap alignment clamp.

In preference the front plate is mountable, separable from and/or to the generally L shaped femoral tibia stability gap alignment clamp.

In preference the front plate and the base plate are a single piece wherein the single piece forms a generally L shaped configuration.

In preference the base plate includes two separate sections extending out horizontally from the front plate, wherein each separate section of the base plate is positionable below a corresponding user-operable height adjustable extension tab adapted to adjust the vertical height of the respective separated sections of the base plate relative to the horizontal arm of the generally L shaped femoral tibia stability gap alignment clamp.

Hence for the purpose of this invention the generally L shaped femoral tibia stability gap alignment clamp can either be generally a single device or alternatively an arrangement that has an assembly wherein the front plate and base plate is mountable/separable from and/or to the generally L shaped femoral tibia stability gap alignment clamp.

Balancing the femoral side of the prosthetic knee joint with the tibia is complex, in that while the tibial cut is made perpendicular to the tibial shaft, the femur requires correct resection of not only the distal femur but also the posterior femoral condyle.

Advantageously, the unique use of the generally L shaped femoral tibia stability gap alignment clamp provides for the two arms wherein the vertical arm and the associated lateral extension tabs will be responsible for providing the requisite distal valgus angle through the engagement with the front plate, and the horizontal arm with the associated height extension tabs makes the necessary adjustments to the base plate (and/or separate sections of the base plate) to establish the requisite posterior condylar axis rotation so that the posterior femoral condyle of the femur is cut appropriately so that the final resection of each of the distal femur and the posterior femoral condyle then accepts the femoral component of the prosthetic joint with the proper positioning for creating a stability gap for stable balanced angular movement throughout the arc of motion from extension, mid-flexion and flexion of the knee joint post surgery for the patient.

In preference an initially resected end of the femur includes a skim cut of the distal femur and a skim cut of the posterior femoral condyle.

In preference the generally L shaped femoral tibia stability gap alignment clamp is mounted to the initially resected distal femur.

In preference the front plate is mounted to the generally L shaped femoral tibia stability gap alignment clamp such that the user-operable lateral adjustable extension tabs are engageable with an internal side of said front plate and the user-operable height adjustable extension tabs are engageable with an upper side of said base plate.

In preference a tibia component of the prosthetic knee joint is mountable upon a resection proximal surface of the tibia.

Hence the user-operable lateral adjustable extension tabs included in the vertical arm of the generally L shaped femoral tibia stability gap alignment clamp engaging the internal side of the front surface are adjusted to define a balanced first stability extension gap as the measurements are taken at extension, mid-flexion and flexion whereby the measured first stability gap is commensurate with a reference plane established by the front plate so as to establish correct alignment of the valgus angle for balanced stability and the user-operable height adjustable extension tabs included on the horizontal arm of the generally L shaped femoral tibia stability gap alignment clamp engage the upper surface of the base plate, so that the height adjustment of said plurality of user-operable height extension tabs as introduced above defines the second stability gap, or put another way defines a plane for femoral rotation based on height of the height adjustable extension tabs. From this plane a surgeon can reference this plane to perform the definitive resection of the posterior femoral condylar.

In preference the front plate includes a plurality of apertures.

In preference the plurality of apertures are aligned with corresponding slots incorporated upon the vertical arm of the generally L shaped femoral tibia stability gap alignment clamp.

In preference the plurality of apertures on the front plate with the corresponding slots define a passageway, wherein mount supports are restable within the plurality of apertures of the front plate when mounted to the distal femur adapted to maintain the generally L shaped femoral tibia stability gap alignment clamp in the referenced posterior condylar axis.

By this point both the reference plane defined by the orientation of the front plate providing correct alignment of the distal valgus angle so that the distal femur can be resected appropriately and whereby the posterior condylar axis has also been appropriately established so that the posterior femoral condyle can be cut and resected, for correct femoral rotation.

The requirement is now the translation of these established referenced plane and axis to conventional bone resection tooling to actually complete the task of resection.

The person skilled in the art would be well aware of a variety of ways in which the established reference plane of the front plate can then be translated into a commensurate resection of the distal femur.

One such conventional resection will be referenced in the preferred embodiment of the invention to be described shortly hereafter.

Nonetheless any resection of the distal femur will require the removal of the generally L shaped femoral tibia stability gap alignment clamp and the associated front plate.

The problem, which this invention addresses, is that once the generally L shaped femoral tibia stability gap alignment clamp is removed from its mounted position at the distal end of the femur, how then can the referenced posterior condylar axis thereafter then again be re-established so that the appropriate final resection of the posterior femoral condyle can be completed.

Advantageously, final resection of the posterior femoral condyle can be completed as the posterior condylar axis can be conveniently reconstructed once the resection of the distal femur has been completed.

As introduced above the front panel included a series of apertures to align with corresponding slots on the generally L shaped femoral tibia stability gap alignment clamp wherein once both the reference plane of the front panel and the posterior condylar axis have been established by the operation of the extension tabs on both the vertical and horizontal arms of the generally L shaped femoral tibia stability gap alignment clamp, the orientation of the generally L shaped femoral tibia stability gap alignment clamp could be initially set by introducing the mounts that would pass through the apertures and corresponding slots that were then fixed into the initially resected distal femur.

Once the distal femur has been resected these mounts can then be repositioned within the distal femur and the apertures of the front panel and the associated slots are orientated so as to fit up and be supported by the rods within the same orientation such that the referenced posterior condylar axis is again re-established to which then conventional cutting and resection tooling of the posterior femoral condyle can be used and mounted accordingly in alignment with the established posterior condylar axis to complete the requisite final resection.

In preference each lateral adjustable extension tab includes mechanical, hydraulic, electrical, electronic and/or pneumatic drive action.

In preference each height adjustable extension tab includes mechanical, hydraulic, electrical, electronic and/or pneumatic drive action.

Advantageously the generally L shaped femoral tibia stability gap alignment clamp can be adjusted to an infinite number of positions in 3D, in order to establish the resection of both the distal femur and the posterior femoral condyle such that the translation of the reference plane of the alignment of the front panel and the establishment of the posterior condylar axis by vertical adjustment of the user-operable tab extensions on the horizontal arm of the generally L shaped femoral tibia stability gap alignment clamp when replicated as the final bone resections of the distal femur and the posterior femoral condyle provides the necessary surface profile of the distal end of the femur that when the femoral component of the prosthetic knee joint is implanted, it will be configured as to enable balanced stability between the femoral and the tibia components of the prosthetic knee joint throughout the arc of motion from extension, mid-flexion and flexion post surgery.

In a further form of the invention there is provided an arrangement for the preparation of the proximal surface of the distal end of the femur and the posterior femoral condyle of the femur for a femoral component of a prosthetic knee joint, said arrangement including:

a generally L shaped femoral tibia stability gap alignment clamp mountable to the femur such that a vertical arm of the generally L shaped femoral tibia gap alignment clamp is adapted to be contiguous and/or aligned with the distal end of the femur and a horizontal arm of the generally L shaped femoral tibia gap alignment clamp is adapted to be contiguous and/or aligned with a posterior femoral condyle of the femur;

said vertical arm of the generally L shaped femoral tibia stability gap alignment clamp including user-operable lateral adjustable extension tabs, wherein each user-operable lateral adjustable extension tab is adapted to engage a front plate, such that lateral adjustment of the front plate by said plurality of user-operable lateral adjustable extension tabs defines a first stability gap as a measurement taken in each of extension, mid-flexion and flexion, wherein the first stability gap is commensurate with a reference plane defined by the front surface of the front plate, wherein a final bone resection of the distal femur of the femur with the reference plane provides for a plane to which the final resection is cuttable for balanced angular movement between the tibia component and the femoral component of the prosthetic knee joint throughout an arc of motion from extension, mid-flexion and flexion post surgery;

said horizontal arm of the generally L shaped femoral tibia stability gap alignment clamp includes user-operable height adjustable extension tabs adapted to adjust the vertical height of a base plate relative to the horizontal arm of the generally L shaped femoral tibia stability gap alignment clamp, such that vertical height adjustment of said plurality of user-operable height adjustable extension tabs upon the base plate defines a second stability gap as a measurement taken in each of extension, mid-flexion and flexion, wherein the second stability gap is commensurate with a referenced posterior condylar axis defined by the alignment of an underside of the base plate, wherein a final bone resection of the posterior femoral condyle of the femur consistent with the posterior condylar axis provided by the aligned underside of the base plate provides for balanced angular movement between the femoral component and the tibia component of the prosthetic knee joint throughout an arc of motion from extension, mid-flexion and flexion.

In order now to describe the invention in greater detail a preferred embodiment will be presented with the assistance of the following illustrations and accompanying text.

DETAILED DESCRIPTION OF THE DRAWINGS

Figure 1:
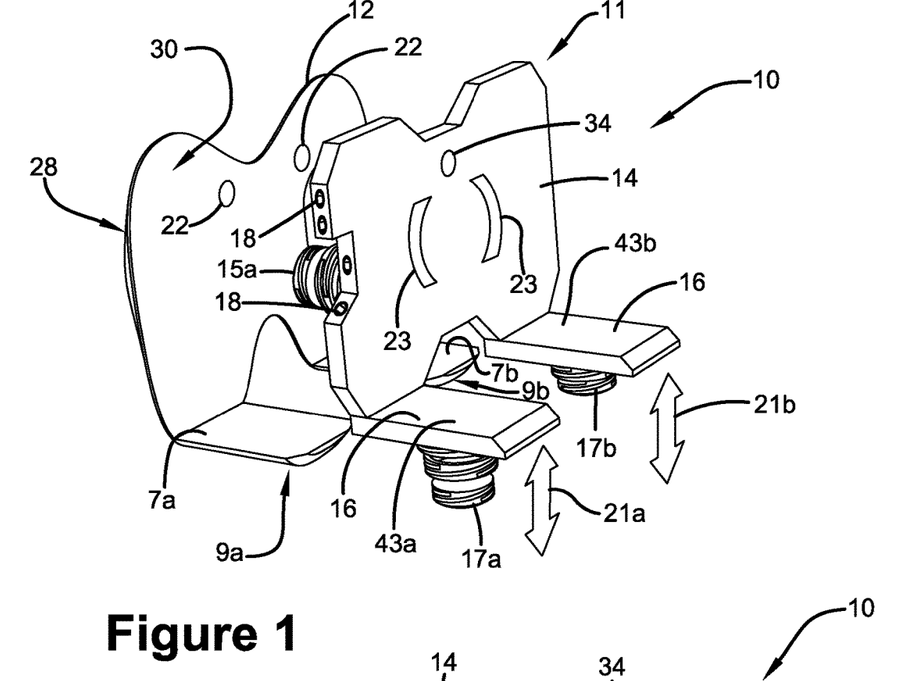
FIG. 1 is a rear perspective view of the arrangement in a preferred embodiment of the invention.
Figure 2:
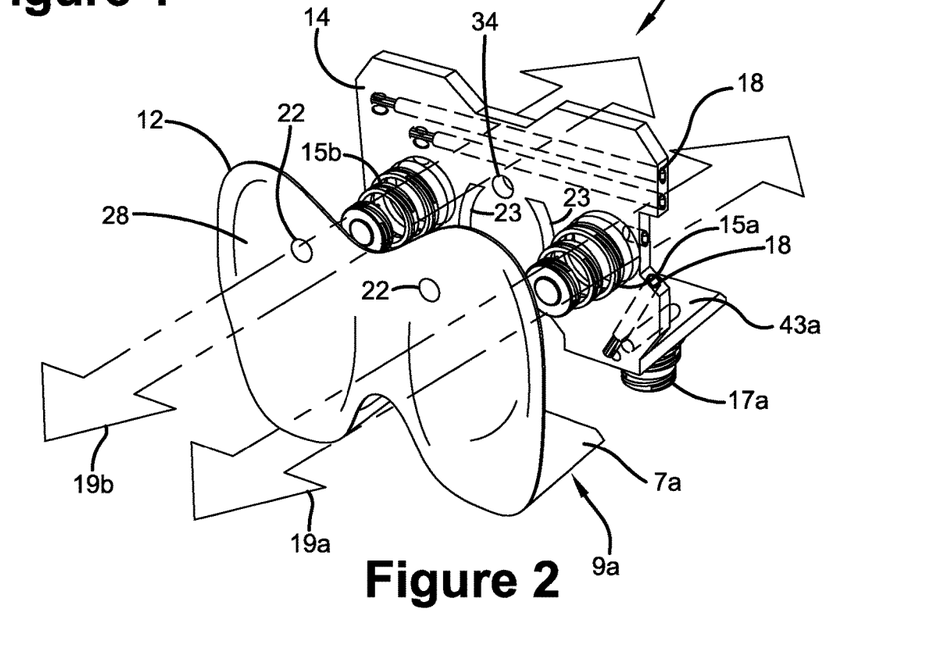
FIG. 2 is a front perspective view of the arrangement in a preferred embodiment of the invention.

FIGS. 1 and 2 show the arrangement (10) that is responsible for the preparation of a bone profile at the end of the femur which will be such that when the femoral component of the prosthetic knee joint is positioned it will work with the tibial component so there will be a balanced stable prosthetic knee joint movement throughout the arc of motion from extension, mid-flexion and flexion.

The arrangement (10) includes the generally L shaped femoral tibia stability gap alignment clamp (11).

In the preferred embodiment the front plate (12) is a separate piece to the generally L shaped femoral tibia stability gap alignment clamp (11).

Figure 3A:
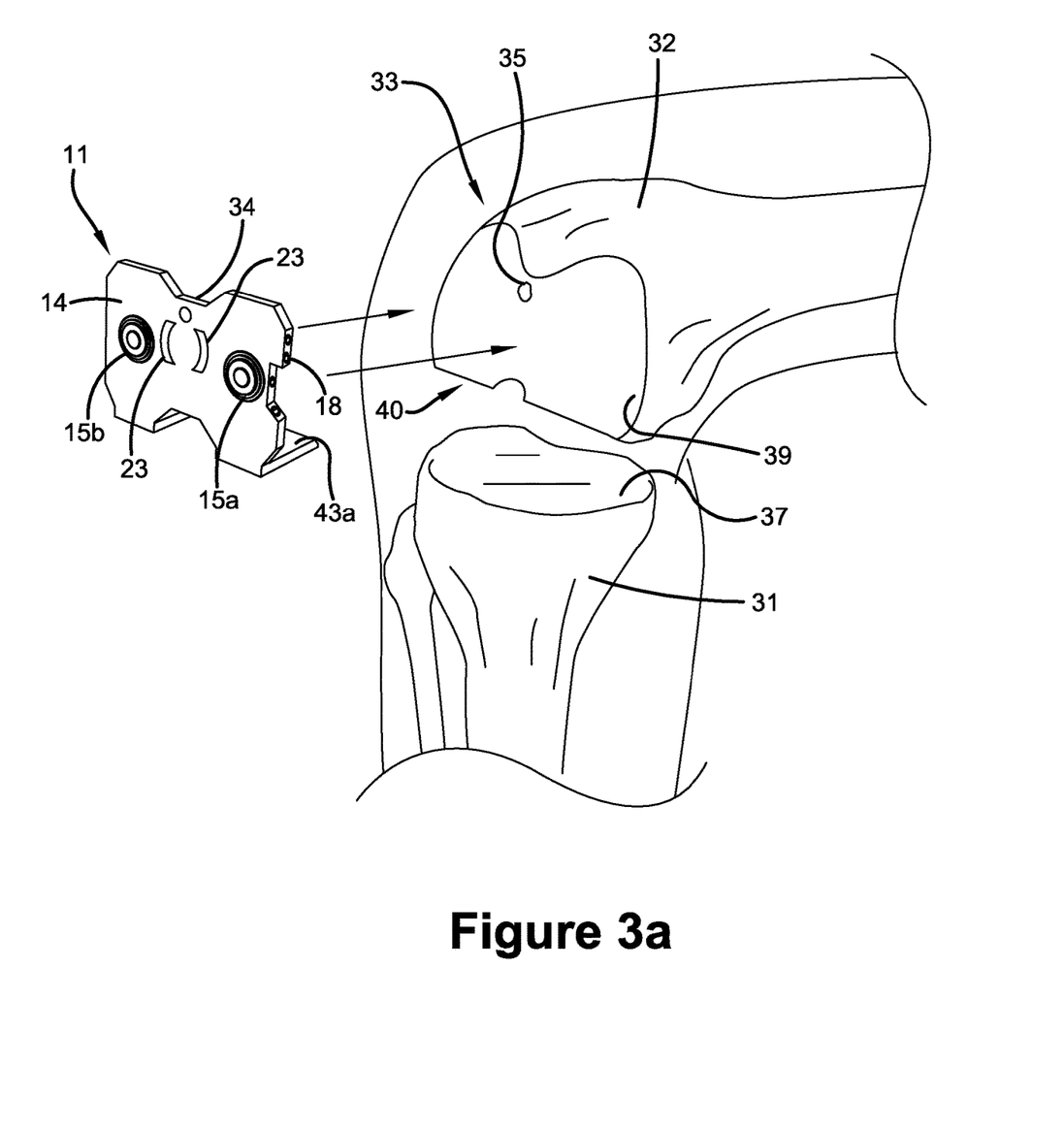
FIGS. 3a, 3b and 3c are schematic representations of a method by which the arrangement can be utilised in order to prepare the distal end of the femur for appropriate final resection of the distal femur and the posterior femoral condyle.
Figure 3B:
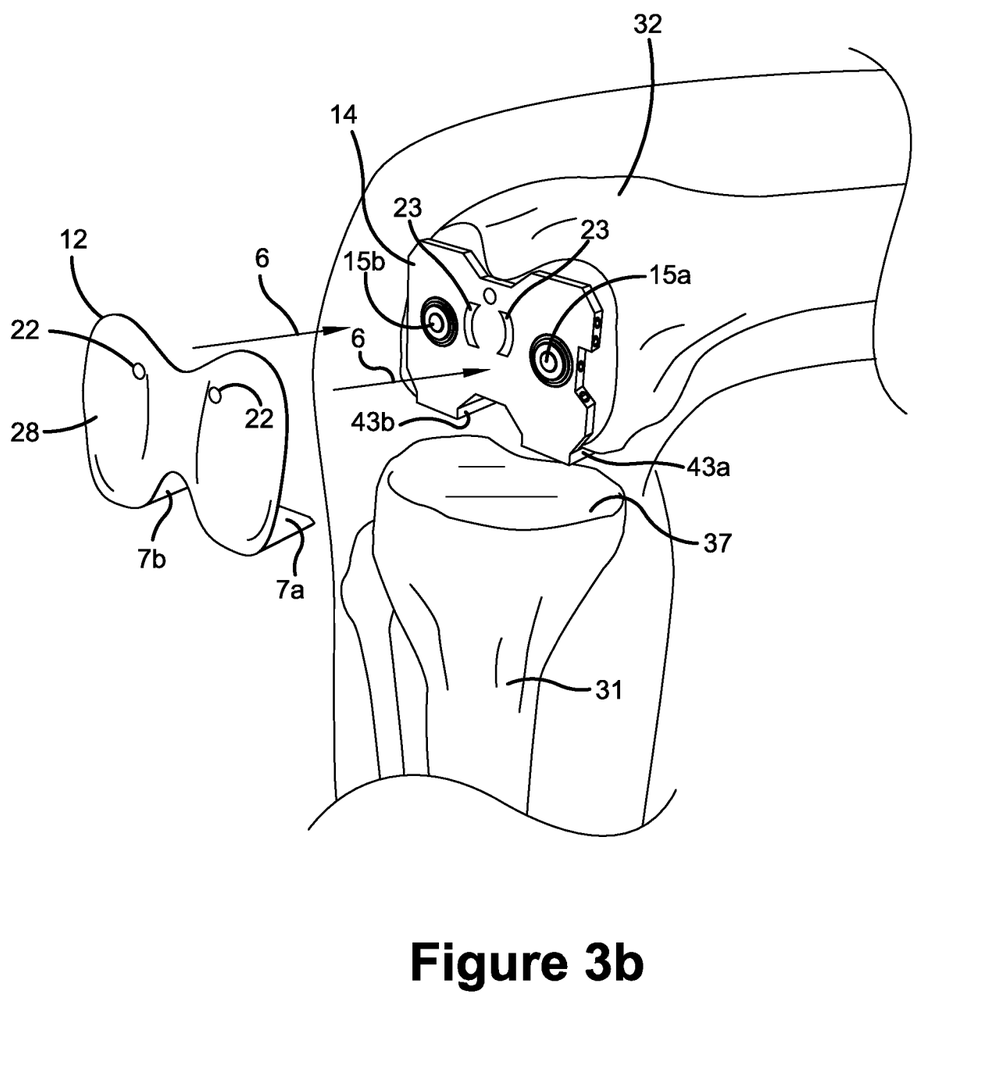
Figure 3C:
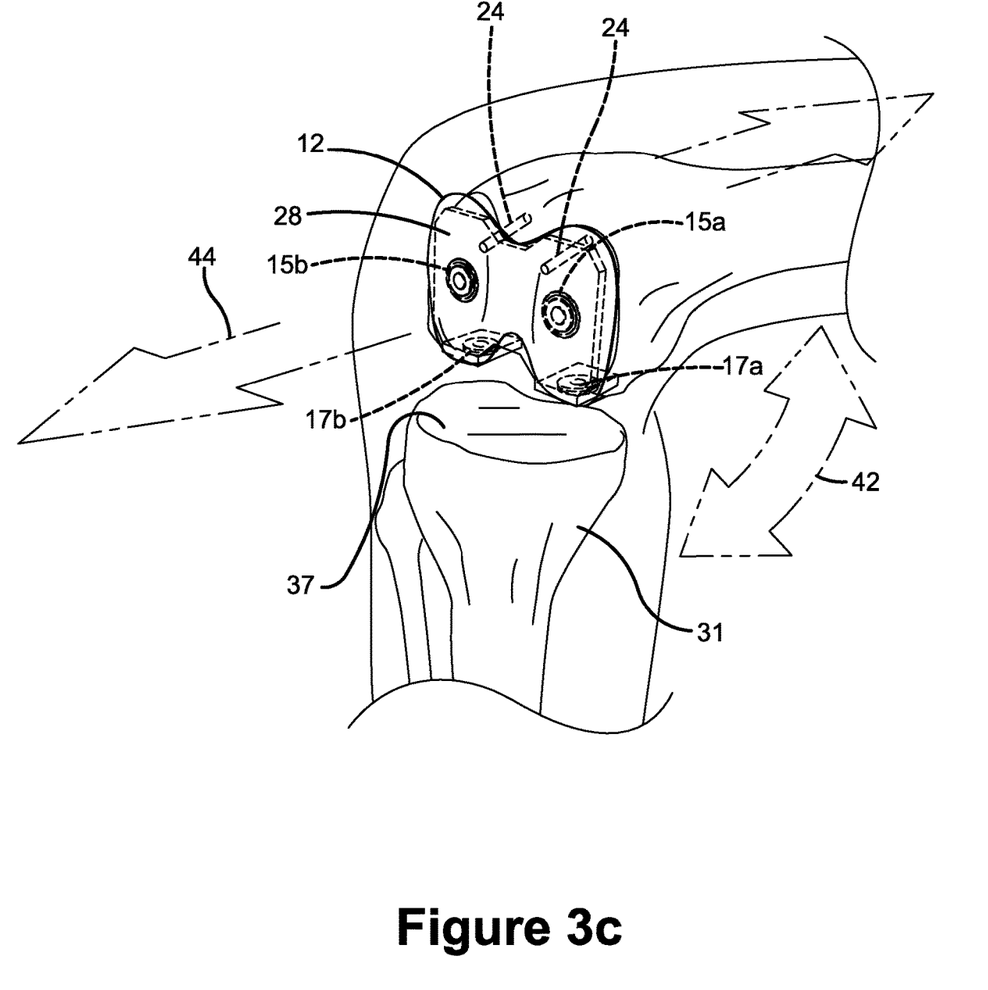

The front plate (12) is commensurate in dimensions with dimensions and shape of the distal end of the femur as best seen in FIG. 3c.

The base plate in the preferred embodiment includes separate sections (7a) and (7b), wherein each section (7a) and (7b) of the base plate is engaging below a corresponding user-operable height adjustable tab (17a) and (17b) on the respective sections (43a) and (43b) of the horizontal arm (16) of the generally L shaped femoral tibia stability gap alignment clamp (11).

In other embodiments not shown the front plate (12) and the base plate (7a) and (7b) can be integral as a single assembly with the generally L shaped femoral tibia stability gap alignment clamp (11).

As best seen in FIGS. 1 and 2 the front plate (12) and the base plate sections (7a) and (7b) are all a single piece wherein the single piece forms a generally L shaped configuration commensurate with the configuration of the generally L shaped femoral tibia stability gap alignment clamp (11).

The horizontal arm (16) as introduced above is in fact two sections (43a) and (43b) so that the horizontal arm (16) is configured generally consistent with the distal end of the femur.

The vertical arm (14) of the generally L shaped femoral tibia stability gap alignment clamp (11) includes the user-operable lateral adjustable tabs (15a) and (15b) which are adapted to engage the internal side (30) of the front plate (12) when the front plate (12) is mounted or connected to the generally L shaped femoral tibia stability gap alignment clamp (11).

In the preferred embodiment shown in FIGS. 1 and 2 there are two of the user-operable height adjustment tabs (17a) and (17b) and two user-operable laterally adjustable tabs (15a) and (15b).

Nonetheless there is no limit to the amount and/or orientation of the user-operable height and lateral adjustable extension tabs for this invention.

As will be discussed in greater detail shortly hereafter, the scope of the invention simply provides for incorporating a plurality of user-operable lateral extension tabs on the vertical arm (14) and the same too for a plurality of height adjustable extension tabs on the underside of the horizontal arm (16) of the generally L shaped femoral tibia stability gap alignment clamp (11).

As will be explained in greater detail the height adjustability shown by way of arrows (21a) and (21b) in FIG. 1 for the height adjustable extension tabs (17a) and (17b) along with the lateral adjustability of the user-operable lateral extension tabs (15a) and (15b) in FIG. 2 shown by way of arrows (19a) and (19b) will provide for the appropriate orientation of the arrangement (10) such as to establish the requisite distal valgus angle to complete the final resection of the distal end of the femur and the requisite posterior condylar axis rotation for the appropriate final resection of the posterior femoral condyle.

The front plate (12) also includes apertures (22) which when the front plate (12) is mounted to the generally L shaped femoral tibia stability gap alignment clamp (11) align with the arched slots (23), mounting rods (24) can be used then to mark out the way in which the posterior condylar axis can be re-established.

The preferred embodiment shows a series of slots (18) to which requisite tooling can engage in order to laterally and vertically adjust the lateral extension tabs (15a), (15b) and/or height adjustable extension tabs (17a) and (17b), again in the arrowed directions shown as (19a), (19b) or (21a) and (21b).

The positioning and operation of the slots (18) is not essential to the invention and can be achieved through a variety of design choices and tool operation to drive the lateral extension tabs (15a), (15b) and/or height adjustable extension tabs (17a) and (17b) in the arrowed directions shown as (19a), (19b) or (21a) and (21b), including mechanically, hydraulically, electrically, electronically and/or through computer navigation, robotics or a pneumatic drive action arrangement.

The slots (18) simply signify that the relevant laterally adjustable extension tabs (15a) and (15b) and the height adjustable extension tabs (17a) and (17b) can be manipulated accordingly in order to spherically orientate the front plate 12 and the sections (7a) and (7b) of the base plate relative to the generally L shaped femoral tibia stability gap alignment clamp (11) so that the established valgus angle and the posterior condylar axis can be referenced and then resected to those referenced orientations and/or alignments of the front surface (28) of the front plate and the undersides (9a) and (9b) of sections (7a) and (7b) of the base plate for the correct positioning of the femoral component of the knee joint to the femur.

Referring now to FIGS. 3a, 3b and 3c.

In FIG. 3a, presented is the femur (32) and tibia (31).

The distal end (33) of the femur (32) has had two skim cuts made. These include initial resection at the end (33) of the femur (32) shown as (39) and the posterior femoral condyle (40).

The generally L shaped femoral tibia stability gap alignment clamp (11) is mounted to the initially resected skim cut surface (39) at the distal end (33) of the femur (32).

A bore hole (35) is shown which correlates with a hole (34) through the vertical arm (14) of the generally L shaped femoral tibia stability gap alignment clamp (11).

This simply is meant to be illustrative that the generally L shaped femoral tibia stability gap alignment clamp (11) is mountable to the distal end (33) of the femur (32) such that the vertical arm (14) aligns with the initially resected skim cut surface (39) and the horizontal arm (16) and corresponding base plate sections (7a) and (7b) aligns with the posterior femoral condyle (40).

In some literature the posterior femoral condyle is referred to as the posterior femoral condyles reflective of the two opposing sides however in this invention the posterior femoral condyle is referred to collectively and so too generally the horizontal arm (16) of the generally L shaped femoral tibia stability gap alignment clamp (11) by way of in fact the two separate sections (43a) and (43b) are included as part of the single arm (16) reference.

In the preferred embodiment shown in FIG. 3b, once the generally L shaped femoral tibia stability gap alignment clamp (11) is mounted to the femur (32) the front plate (12) can then be mounted to the generally L shaped femoral tibia stability gap alignment clamp (11) according to the engagement shown by way of arrows (6) with the actual mounting shown in FIG. 3c.

Though not shown in FIG. 3c when the measurements are taken there is a removal tibial component (not shown) resting on the tibia surface 37 of the tibia 31 to represent the tibia prosthetic component so that the stability gap between the femoral and tibia components can be measured.

In FIG. 3c arrow (42) is reflective as to how the vertically adjustable extension tabs (17a) and (17b) can be manipulated so that the orientation of the sections (7a) and (7b) of the base plate can be aligned.

The sections (43a) and (43b) of the horizontal arm (16) of the generally L shaped femoral tibia stability gap alignment clamp (11) includes the user-operable height adjustable extension tabs (17a) and (17b) and these adjust the vertical height of the base plate relative to the sections (43a) and (43b) of the horizontal arm (16) of the generally L shaped femoral tibia stability gap alignment clamp (11), such that vertical height adjustment of the user-operable height adjustable extension tabs (17a) and (17b) upon sections (7a) and (7b) of the base plate provides a stability gap as a measurement taken in each of extension, mid-flexion and flexion, wherein this stability gap is commensurate with a referenced axis or plane defined on the undersides (9a) and (9b) of sections (7a) and (7b) of the base plate, wherein final bone resection with the provided for referenced axis or plane defined on the undersides (9a) and (9b) of sections (7a) and (7b) of the base plate to the posterior femoral condyle (40) of the femur (32) provides for surface that will allow balanced angular movement between the femoral component and the tibia component of the prosthetic knee joint throughout an arc of motion from extension, mid-flexion and flexion.

However as well as establishing the referenced axis or plane defined on the undersides (9a) and (9b) of sections (7a) and (7b) of the base plate to provide for the alignment of the definitive final resection to the posterior femoral condyle (40) of the femur (32), there will also be the requirement to make available the most appropriate distal valgus angle to the surface (39) at the distal end (33) of the femur (32) and this is achieved through the lateral adjustment of the user-operable lateral extension tabs (15a) and (15b) on the vertical arm (14) of the generally L shaped femoral tibia stability gap alignment clamp (11).

Effectively the front surface (28) of the front plate (12) once it has been laterally manipulated by the user-adjustable lateral extension tabs (15a) and (15b) shown by way of arrow (44), this will then create a reference plane which in effect is just the stability gap measurement that was taken by laterally adjusting the user-operable lateral extension tabs (15a) and (15b) of the taken measurements at extension, mid-flexion and flexion.

This reference plane defined by the alignment or orientation of the front surface (28) of the front plate (12) established by the measurements taken, means that if the same reference plane defined by the alignment or orientation of the front surface (28) of the front plate (12) is used to complete the definitive final resection cut to the surface (39) of the distal end (33) of the femur (32) then this will assist in establishing the best possible stability and balance to the prosthetic knee joint post surgery.

FIG. 3c represents the completion of the measurements taken at extension, mid-flexion and flexion such that the orientation of the generally L shaped femoral tibia stability gap alignment clamp (11) has been completed for appropriate determination of the posterior condylar axis resection and the orientation of the reference plane established by the front plate (12) for the correct valgus angle.

Once the distal end (33) of the femur (32) has been definitively resected at surface (39) then the reference axis or plane that provides the alignment or orientation for the definitive resection cut of the posterior femoral condylar (40) is reconstructed.

This is achieved by mounting rods (24). Mounting rods (24) were mounted prior to the definitive resection cut of the surface (39) for distal end (33) of the femur (32) but removed subsequently before the final resection.

Once the requisite reference posterior femoral condylar axis or plane has been established and the generally L shaped femoral tibia stability gap alignment clamp (11) has been orientated, this will be reflected by the way in which the front plate (12) and the base plate sections (7a) and (7b) are orientated.

To make reproducible the reference posterior femoral condylar axis or plane that provides the alignment or orientation for the definitive resection cut of the posterior femoral condylar (40) the mounting rods (24) can again be mounted into the end (33) of the distal femur (32).

The bore holes (not shown) for the mounting rods (24) would be deep enough into the distal end (33) of the femur (32) so that the final resection of the surface (39) at the distal end (33) of the femur (32) would not extend beyond the depth of the bore holes (not shown) in which the mounting rods (24) would be mounted therein.

When the distal end (33) of the femur (32) needs to be cut, conventional cutting mechanisms can be used wherein the cutting tool or assembly (not shown) would be mounted up against the orientated front plate (12) to provide for the same reference plane to establish the distal valgus angle.

Once the cutting equipment is in place there would then be the requirement to remove the generally L shaped femoral tibia stability gap alignment clamp (11) to complete the clean definitive final resection of the distal femur.

Again, the mounting rods (24) can be re repositioned back into the distal femur holes for conventional cutting means to then be used to take that referenced posterior femoral condylar axis or plane and then move it back into clean femur bone in order to make the requisite final cut with the appropriate orientation of the posterior condylar axis or plane which was established by the measurements that were taken at extension, mid-flexion and flexion previously.

Advantageously the arrangement of the invention allows the surgeon to adjust the position of the femoral component of the prosthetic knee joint following two initial skim cuts to the distal femur and the posterior femoral condyle so as to mount the generally L shaped femoral tibia stability gap alignment clamp (11). This then allows the surgeon to attach the front plate (12) including the base plate sections (7a) and (7b) which replicates the shape of the implant.

The surgeon can then adjust the user-operable lateral extension tabs (15a) and (15b) on the vertical arm (14) of the generally L shaped femoral tibia stability gap alignment clamp (11) to obtain perfect balance in extension, mid flexion and flexion, wherein the reference plane established on the front surface (28) of the front plate (12) defines the desired distal femoral vertical arm to balance the knee.

Then the surgeon can the adjust the user-operable height extension tabs (17a) and (17b) on the sections (43a) and (43b) of the horizontal arm (16) of the generally L shaped femoral tibia stability gap alignment clamp (11) to obtain the referenced posterior femoral condylar axis or plane which when the posterior femoral condylar surface (40) is definitively resected in the alignment provided by the referenced posterior femoral condylar axis or plane optimal rotation of the implant and balance throughout the arc of motion for the knee joint becomes available post surgery.

Advantageously the arrangement allows a surgeon to adjust the femoral component in an infinite number of ways to obtain a desired "3D" position to balance the knee joint appropriately.

The invention claimed is:

1. An arrangement for providing a proximal surface of a distal end of a femur and a posterior femoral condyle of the femur for a femoral component of a prosthetic knee joint, said arrangement including:
   a generally L shaped femoral tibia stability gap alignment clamp mountable to the femur such that a vertical arm of the generally L shaped femoral tibia gap alignment clamp is contiguous and aligned with the distal end of the femur and a horizontal arm of the generally L shaped femoral tibia gap alignment clamp is contiguous and aligned with the posterior femoral condyle of the femur;
   a front plate;
   wherein said vertical arm of the generally L shaped femoral tibia stability gap alignment clamp includes a plurality of independently adjustable user-operable lateral adjustable extension tabs that engage an internal surface of the front plate, such that independent lateral adjustment of the front plate by each of the plurality of independently adjustable user-operable lateral adjustable extension tabs at extension, mid-flexion and flexion defines a first stability gap commensurate with a first reference plane defined by the front surface of the front plate, the independent lateral adjustment being based on gap measurements taken at extension, mid-flexion and flexion;
   a base plate;
   wherein the front plate and the base plate are connected orthogonally, such that they create a generally L shaped configuration commensurate with the generally L shaped femoral tibia stability gap alignment clamp;

wherein said horizontal arm of the generally L shaped femoral tibia stability gap alignment clamp includes a plurality of independently adjustable user-operable height adjustable extension tabs that engage an upper side of the base plate, such that independent vertical height adjustment of the base plate by each of the plurality of independently adjustable user-operable height adjustable extension tabs, at extension, mid-flexion and flexion, defines a second stability gap commensurate with a second reference plane defined on an underside of the base plate, the independent lateral adjustment being based on gap measurements taken at extension, mid-flexion and flexion; and wherein a final bone resection with the first reference plane to bone at the distal end of the femur and a final bone resection with the second referenced plane to bone of the posterior femoral condyle of the femur provides for balanced angular movement between a tibia component and the femoral component of the prosthetic knee joint throughout an arc of motion from extension, mid-flexion and flexion post surgery.

2. The arrangement of claim 1 wherein the base plate includes a base plate first section and a base plate second section, wherein the base plate first section and the base plate second section are positioned below a corresponding independently adjustable user-operable height adjustable extension tab wherein each corresponding independently adjustable user-operable height adjustable extension tab extends from the horizontal arm of the generally L shaped femoral tibia stability gap alignment clamp.

3. The arrangement of claim 1 wherein the generally L shaped femoral tibia stability gap alignment clamp is mounted to an initially resected distal femur.

4. The arrangement of claim 1 wherein the front plate includes a plurality of apertures.

5. The arrangement of claim 4 wherein the plurality of apertures are aligned with corresponding vertical slots incorporated upon the vertical arm of the generally L shaped femoral tibia stability gap alignment clamp.

6. The arrangement of claim 5 wherein the plurality of apertures on the front plate with the corresponding vertical slots define a passageway, wherein mount supports are passable therethrough for reconstructing the orientation of the second reference plane.

7. The arrangement of claim 1 wherein each independently adjustable user operable lateral adjustable extension tab and each independently adjustable user operable height adjustable extension tab includes mechanical, hydraulic, electrical, electronic, computer navigation, robotics or pneumatic drive action.

8. The arrangement of claim 1 wherein the front plate includes a front plate first section and a front plate second section, wherein the front plate first section and the front plate second section of the front plate each engage separate independently adjustable user-operable lateral adjustable tabs, wherein each of the separate independently adjustable user-operable lateral adjustable tabs are extendable out from vertical arm of the generally L shaped femoral tibia stability gap alignment clamp.

\* \* \* \* \*